United States Patent
Brown

(10) Patent No.: US 10,383,772 B2
(45) Date of Patent: Aug. 20, 2019

(54) SKIN PROTECTION DEVICE

(71) Applicant: Richard Charles Brown, Bushey (GB)

(72) Inventor: Richard Charles Brown, Bushey (GB)

(*) Notice: Subject to any disclaimer, the term of this patent is extended or adjusted under 35 U.S.C. 154(b) by 748 days.

(21) Appl. No.: 14/762,945

(22) PCT Filed: Jan. 15, 2014

(86) PCT No.: PCT/GB2014/050111
§ 371 (c)(1),
(2) Date: Jul. 23, 2015

(87) PCT Pub. No.: WO2014/114913
PCT Pub. Date: Jul. 31, 2014

(65) Prior Publication Data
US 2015/0374554 A1   Dec. 31, 2015

(30) Foreign Application Priority Data
Jan. 24, 2013  (GB) .................................... 1301230

(51) Int. Cl.
*A61F 13/04*   (2006.01)
*A61F 15/00*   (2006.01)
(Continued)

(52) U.S. Cl.
CPC .......... *A61F 13/02* (2013.01); *A61F 13/0226* (2013.01); *A61F 13/0246* (2013.01);
(Continued)

(58) Field of Classification Search
CPC .... A61F 13/02; A61F 13/0226; A61F 13/041; A61F 15/004; A61F 2013/00089;
(Continued)

(56) References Cited

U.S. PATENT DOCUMENTS 2,558,367 A * 6/1951 Madsen ................. A44B 19/16
                                                      138/128
2,772,712 A * 12/1956 Post ........................ A24F 23/02
                                                      383/65
(Continued)

FOREIGN PATENT DOCUMENTS

DE          3602632 A1     7/1987
GB         1301230.7 A    12/1972
(Continued)

OTHER PUBLICATIONS

Kong, M., Li, W., Li, H., Liu, X. and Zhou, Z., 2008. The skin frictional properties of 4 kinds of commonly used prosthetic materials. Sheng wu yi xue gong cheng xue za zhi= Journal of biomedical engineering= Shengwu yixue gongchengxue zazhi, 25(5), pp. 1107-1111.*

(Continued)

*Primary Examiner* — Kari K Rodriquez
(74) *Attorney, Agent, or Firm* — Bacon & Thomas, PLLC

(57) ABSTRACT

The present invention relates to a skin protection device comprising: a flexible cover having a first end and a second end. The cover comprises two sides extending between said first and second ends. The sides comprise seal sections capable of mutual engagement to form a seal. Each seal section includes a surface that is longitudinally serrated or undulating, wherein serration or undulation is provided on both sides of the section, a first female serrated or undulating side and a second male serrated or undulating side which when placed together form a mating pair and the seal. Each seal section is an extrusion as one part with a flat base and a plurality of serrations or undulations, folded and secured around the sides of the cover so that the flat base is in contact with both surfaces of the cover.

6 Claims, 4 Drawing Sheets

(51) Int. Cl.
*A61F 13/02* (2006.01)
*A61F 13/00* (2006.01)

(52) U.S. Cl.
CPC .......... *A61F 13/041* (2013.01); *A61F 15/004* (2013.01); *A61F 2013/004* (2013.01); *A61F 2013/00089* (2013.01)

(58) Field of Classification Search
CPC .............. A61F 2013/004; A61F 13/208; A61F 2013/0089; A61F 2013/0093; A61F 2013/00102; A61B 46/00; A61B 46/20; A61B 46/23; A61B 46/27; A61B 1/00135; Y10T 24/2532; Y10T 24/2538; Y10T 156/1034; A61K 9/7069; A44B 18/00; A44B 19/10; A44B 19/16; F16B 5/00; B29L 2031/003; B29C 47/003; B29C 53/04
USPC .......... 24/585.1, 452; 383/63; 156/217, 227, 156/244.25
See application file for complete search history.

(56) References Cited

U.S. PATENT DOCUMENTS

| | | | | |
|---|---|---|---|---|
| 4,153,054 | A * | 5/1979 | Boone | A61B 46/27 128/856 |
| 5,212,855 | A * | 5/1993 | McGanty | A44B 18/0046 24/452 |
| 5,807,300 | A * | 9/1998 | Nix, Jr. | A61F 15/004 602/79 |
| 6,210,352 | B1 * | 4/2001 | Williams | A61F 15/004 128/849 |
| 6,511,562 | B1 * | 1/2003 | Coffield | A47C 4/30 156/196 |
| 6,659,970 | B1 * | 12/2003 | Woodworth | A61F 15/004 128/888 |
| 6,974,428 | B2 * | 12/2005 | Knutson | A61F 15/008 602/2 |
| 7,955,284 | B2 | 6/2011 | Brown et al. | |
| 2005/0027227 | A1 | 2/2005 | Dumas et al. | |
| 2005/0251973 | A1 * | 11/2005 | Sprehe | B65D 33/2541 24/399 |
| 2010/0305485 | A1 | 12/2010 | Gaffney | |
| 2012/0036733 | A1 * | 2/2012 | Dehn | A61F 13/00008 34/282 |
| 2014/0074010 | A1 * | 3/2014 | Veres | A61N 5/06 604/20 |

FOREIGN PATENT DOCUMENTS

| | | |
|---|---|---|
| GB | 2443391 A1 | 5/2008 |
| WO | 9526909 A1 | 10/1995 |
| WO | 9811856 A1 | 3/1998 |

OTHER PUBLICATIONS

Patent Cooperation Treaty's Written Opinion of the International Searching Authority for PCT/GB2014/050111.
Letter dated Jun. 18, 2013 from the Intellectual Property Office regarding GB1301230.7.

* cited by examiner

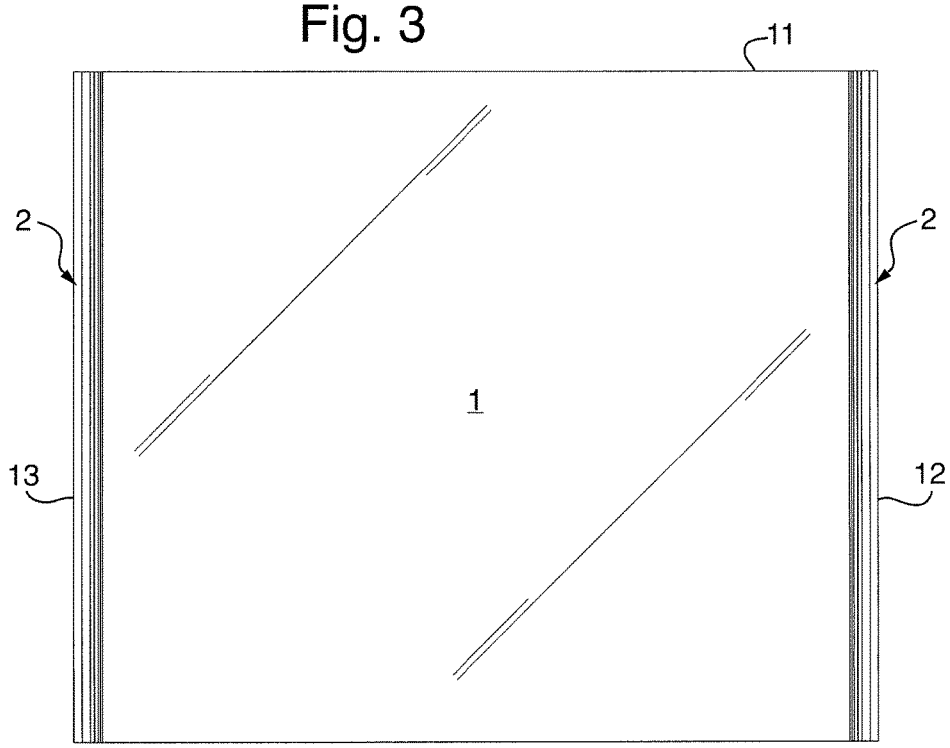
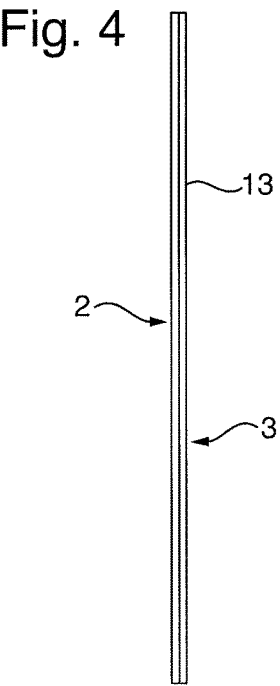

SKIN PROTECTION DEVICE

FIELD OF THE INVENTION

The present invention relates to a skin protection device, more particularly, but not exclusively, a device for covering and chemically protecting ruptured or damaged skin and/or to protect a dressed wound from moisture.

BACKGROUND

If skin is damaged or irritated it may be necessary to keep it clean, bacteria free, dry or moist and to keep the dressing which may or may not protect it in the appropriate condition. At times this may be difficult for example whilst washing or showering, if it is raining, if heat or sunlight is present, or if a wound site is exposed to adverse surrounding elements such as bacterial infection or potentially threatening substances like soil and the like.

Typically a user will be required to keep the afflicted part of their body away from water or have a need to retain moisture around a wound site. However, if protection from water or heat or adverse substances is required for prolonged periods of time, this may not be possible. Therefore, the afflicted part of the body must be covered to provide protection.

Waterproof tape or plasters may be provided, however, such means may not be suitable for larger areas of the body such as an abdomen, arm or leg. Adapted bags may be provided to be worn over a limb, however, these may be difficult to fit with one hand, uncomfortable, cumbersome, expensive and typically can only be used once.

Some waterproof dressings are available to cover large areas, however, it may not be possible to establish if the wound or dressing remains dry once it has been covered, so the user must be cautious. Furthermore, it may not be possible for existing dressings to adapt to the user's movements and adverse climatic or artificial conditions.

The present invention, at least in a preferred embodiment, seeks to overcome the problems associated with protecting damaged skin which must be kept infection free, moist to promote healing or dry to protect a wound dressing.

PRIOR ART

U.S. Pat. No. 6,210,352 discloses a splash-proof limb sleeve which comprises two silicone seals which are provided at each end of a protective cover. Each silicone seal comprises a rib towards one end of the seal and a groove towards the other end of the seal and is arranged so that it can be joined to itself around a limb by accommodating the rib in the groove.

SUMMARY OF THE INVENTION

In a first aspect, the present invention provides a skin protection device comprising: a flexible cover having a first end and a second end with two sides extending therebetween, wherein said sides comprise seal sections, wherein said seal sections are capable of mutual engagement to form a seal wherein each seal section includes a surface that is longitudinally serrated or undulating, and wherein serration or undulation is provided on both sides of the section, a first female serrated or undulating side and a second male serrated or undulating side which when placed together form a mating pair and the seal.

In contrast to the above described known arrangements, the present invention, at least in a preferred embodiment, provides a quick and easy to use, highly flexible means of protecting skin as, when and where required. In particular, the present invention may be able to lock moisture out or in and provide various chemical based protection inclusions to address a range of bacterially adverse or naturally occurring climatic and man-made conditions.

The present invention may provide a continuous seal and closure which may fit any size appendage of a patient. This means that the present invention may provide a single skin protection device which provides a seal and closure to fit any size. Owing to the fact that the skin protection device may fit any size appendage, healthcare users may able to operate with fewer wound dressings.

The present invention allows the integration of a closure and a waterproof seal in one device. The device may be applied by the user with one hand and once applied may remain in firm contact with a user's skin. Each seal section engages with itself to form the seal when the seal sections are overlapped on themselves The seal sections may be shaped in such a way as to encourage liquid to disperse from the wound site and/or to overcome slight undulations in the skin or bone so that a tight moisture-proof seal is maintained during use. Furthermore, said sections may come into contact with the skin over a low, i.e. small, surface area. This means that it is possible to improve comfort and cause less damage to a user's wound site than traditional adhesives or tapes.

The device may comprise an elongate length of flexible cover. The first and second ends may be open ends.

The device therefore comprises a cover that in use may be capable of forming a waterproof cover and seal over or around skin, such as skin that is damaged or dressed in some way, so as to be able to prevent or reduce extraneous substances polluting or reaching the skin, or inhibiting or damaging a dressing. Alternatively, or additionally, the device may be used to lock moisture into the wound site, to keep substances or bacteria from entering or leaving the wound site, to provide topical treatments to the wound site pre- or post-surgical or medical intervention, or to guard against physical or chemical trauma to the skin or body part. The device may also be used to protect minor cuts, burns and grazes.

The device may also be used on deceased patients. In this application the device may be used to protect wound sites for later forensic investigations.

The device may be arranged in use to provide a protective layer for the skin. In an embodiment, the device comprises a flexible cover with hydrochromic means. The cover may be arranged in use to be fastened or secured to the user, e.g. the skin of the user, by the seal sections.

In an embodiment, the seal sections each comprise at least one substantially peripheral sealing strip. The at least one sealing strip may be arranged to extend along at least a portion of the peripheral edge of its respective side. The at least one sealing strip may be an elongate sealing strip. Each strip or seal may be arranged in use to adhere to, or simply be in firm contact with, the skin or to another portion of the flexible cover, such as, for example, another portion of the seal.

In this way the protective cover may be used to cover parts of a user's body or skin or a wound dressing which requires protecting from water or extraneous liquid, for example a wound, dressed wound, rash, new tattoo or where a wound site needs to be kept moist such as a burn or ulcer or a pre- and post-surgical or medical intervention site.

Advantageously, the skin protection device (or protective cover) may be cut to size and wrapped around a relevant part of the user, for example, their arm, leg or abdomen.

In an embodiment, the device may comprise a wound care product, such as a lattice patch, an absorbent dressing material or any other form of patch, which is attached, such as by adhesive, to one surface of the flexible cover. For example, a wound care product may have a self-adhesive back which can be stuck to one surface of the cover (the surface which faces the patient's skin during use). In this embodiment, when the device is applied and sealed around a part of a patient, the wound care product can be held in contact with the wound by the device. Further the device protects the wound care product from water and mechanical damage. This embodiment means that it is not necessary to use adhesive to hold the wound care product on the patient and the device effectively acts as a carrier for a wound care product.

In embodiments the cover is a thin, deformable, robust and/or waterproof film that may be positioned over the wound in order to prevent it, or any subordinate associated dressing, becoming wetted, for example whilst showering. Alternatively, the cover may maintain the wound site in an environment that needs to be kept moist and/or chemically protected from, for example, bacteria, ultra violet and/or manmade substances. In another alternative, the cover may be used to protect other people by containing a bacterial infection.

In an embodiment, the cover is formed from a lightweight, water resistant, flexible material such as a synthetic polymer. The polymer used for the cover may be of medical grade so as to be suitable for use on damaged or broken skin. However, for covers that protect wound sites exclusively, but not limited to getting wet, for some applications non-medical grade polymer may be advantageous for cost reasons. The flexible cover may be cast or may be a blown film extrusion or it may be manufactured by any other known, suitable, manufacturing method.

The cover may be transparent or translucent, at least in part, so that the user is able to see the wound or skin whilst positioning and securing the protective device, thereby ensuring that the wound is fully protected. Some embodiments may comprise a cover which is coloured for aesthetic, user preference, or medical purposes.

The cover may be arranged to act as a filter and/or a magnifier for rays which pass through the cover. The cover may also act to diffuse, disperse or diffract light. For example, the cover may be coated or printed with a layer which allows only particular frequencies of the electromagnetic spectrum to pass through. The cover may additionally, or alternatively, be arranged to magnify and/or disperse rays as they pass through the device. This may allow specific areas of the body to be targeted for radiography or other treatments or medical processes, such as x-ray imaging.

The skin protection device may comprise an outer cover. The outer cover may be opaque. When the device comprises a transparent or translucent flexible cover, it may be desirable to provide an outer cover so as to prevent (or at least reduce) the user being able to see their wound. The outer cover may be attachable (and optionally detachable) to the other parts of the skin protection device, such as via the seal sections.

When the outer cover is detachable and the flexible cover is transparent or translucent, the outer cover may be removed so that the wound can be inspected without having to remove the flexible cover. This can reduce the risk of the wound becoming infected (as the wound is kept in a sealed environment whilst healing) and/or can reduce damage to the wound during healing due to removal of the flexible cover which may damage repairing skin. The cover may be detached and reattached to the other parts of the skin protection device a plurality (a large number or an indefinite number) of times.

The outer cover may comprise engagement sections for engagement with the other parts of the skin protection device. For example, the engagement sections may be longitudinally extending serrations or undulations which can engage with the outwardly facing (in use) surface of the seal sections. The engagement sections may have at least one face which is complementary with a surface of the seal sections.

Advantageously, in some embodiments, a hydrochromic means is provided in, or on, the cover. For example, the hydrochromic means may be provided on the inside face of the cover i.e. the face which, in use, is adjacent to the user's skin, so as to indicate the presence of water underneath the cover.

The hydrochromic means may be hydrochromic ink located on the inner face of the cover, which changes its visual appearance in response to water by changing colour. This means that the device may be capable of revealing if water has penetrated the protective cover or signalling that moisture is present in the cover.

The device may comprise topical treatments. Topical treatments may be, but are not limited to, pain relief, antibiotic, other drug based and or cosmetic based ointments, creams, sprays, and integral polymer based additives such as antimicrobial, ultra violet and anti-corrosive inhibitors. These topical treatment layers may be printed or sprayed onto the films or applied by any other known method. In an embodiment, the topical layers may be arranged so that they are activated by application of moisture, such as perspiration. Thus, a topical layer may be applied and activated when the device is applied to a patient due to perspiration being present within the sealed environment.

Condensation contained within the device in use, due to perspiration and skin moisture may be used to keep a wound moist and bacteria free.

Advantageously, therefore, said hydrochromic means may serve to easily and effectively advise a user if water is detected under the cover so that the user can remove themself from the water source, replace and/or reseal the protective cover and/or have peace of mind that moisture is present at the wound site. The hydrochromic means may only be required, and thus only located, proximate the edges of the cover. This means that production costs may be minimised thereby offering an affordable protection device.

Conversely, in some further embodiments the protective device may be used to maintain moist conditions under the cover to ensure a wound remains moist and does not dry out. The hydrochromic means may, therefore, be used to indicate that the wound remains moist or at a required moisture level, wherein changes in visual appearance serve to advise the user if their wound is drying out. For example, there is much research to suggest that all wounds heal more quickly when kept moist but specifically, and not limited to, burn wounds where it may be especially beneficial for the wound to remain moist to aid optimal healing.

In some embodiments the hydrochromic ink may be provided as a pattern, individual marks or as text or an image which change colour, or becomes visible when exposed to water thereby alerting the user. For example, a raindrop or written statement drawn in hydrochromic ink may become visible if the cover's internal face detects moisture.

In an embodiment, the device, for example the flexible cover, is provided in an elongate strip or rectangular portions so as to have sufficient dimensions to be wrapped around part of the user's body, such as digits or limbs, trunk and waist and to cover the wound. The device may be mounted on and extendable from a reel or spool and optionally provided with a housing which may provide a cutting or cropping means when a desired length of device has been achieved from, i.e. wound off, the spool. The packs, i.e. devices, may be manufactured for one-off domestic applications and/or professional and commercial applications.

When the device is provided on a reel, the reel may be provided in hygienic format, for example with a cowled exit that maintains required hygiene levels, and independent rotation, measurement and cutting means.

In some embodiments the device may be provided in pre-cut shapes for example trapezoid so as to account for tapering in respect of limb shape, for example, a user's wrist being of smaller circumference than the user's forearm.

In embodiments at least one of said seal sections may be enlarged to ensure connection over an offset overlap, wherein the sections may be required to cooperate to form a seal at a myriad of angles. In other words, the serrations or undulations may be arranged so that the seal may be formed even if the seals are mated when at an offset angle relative to each other.

In embodiments two of the cover's opposing edges (sides) include the seal sections, which may serve to connect the cover to the user. At least part of at least one of the seal sections may incorporate shaping so as to overcome slight undulations in the skin or bone so that a tight moisture-proof seal may be maintained. In some embodiments the seal sections may also be dispersed about the cover, comprising plural sites for the seal. At least one of the seal sections may include an adhesive or self-adhesive backing, wherein such sections may be adhered, or displaced and re-adhered, in order to accommodate (and/or affix) an offset cover.

The seal sections may include a surface that is longitudinally serrated or undulating, wherein serration or undulation is provided on both sides of the section, a first female serrated or undulating side and a second male serrated or undulating side which when placed together form a mating pair and a seal. The seal may sandwich along the cover edge (side) in use.

In an embodiment, the seal sections each have complementary opposing surfaces. This means that a first surface of each seal section has a profile which can be received in the other surface of the seal section. This allows one surface of the seal section to create a seal by engagement with the opposing surface of that seal section.

A first surface of each seal section may comprise at least one longitudinally extending peak and the other, a second, surface of the seal section may comprise a corresponding longitudinally extending trough. When the seal sections each comprise at least one longitudinally extending peak and at least one longitudinally extending trough, these form the longitudinal (i.e. longitudinally extending) serrations or undulations.

When the skin protection device is wrapped around a part of a patient's body, so that the ends of the skin protection device overlap, a portion of the at least one longitudinally extending peak may be received in a portion of the corresponding longitudinally extending trough. This means that a seal can be created between the overlapping portions of each seal section. Each seal section mates with itself to form a seal. The first surface of each seal section which comprises a longitudinally extending peak, in use, may be in contact with the user's skin over at least part of its length and may therefore form a seal with the user's skin. Thus a wound can be sealed from an external environment by action of the seal sections each having one surface with a portion forming a seal with the user's skin and also a seal with the opposite surface of the seal section in the overlapping portions.

Alternatively the first surface may comprise at least one longitudinally extending trough and the second surface may comprise the at least one longitudinally extending peak. In the overlapping region the trough may fit onto a peak to form a seal and the peaks either side of the longitudinally extending trough may contact the user's skin to form a seal against the user.

The seal section may comprise any number of longitudinally extending peaks on one surface and the same number of corresponding longitudinally extending troughs on the other surface. When the seal section comprises more than one longitudinally extending peak and corresponding longitudinally extending trough, each longitudinally extending peak and corresponding trough may be of a different size to the other peaks and troughs. For example, the longitudinally extending peak nearest the outer (lateral) side of the seal section (i.e. furthest from the other seal section) flexible cover may have the greatest height and thus the corresponding trough nearest the outer side of the seal section (i.e. the side furthest from the other seal section) would have the greatest (corresponding and/or complementary) depth. The height of the peaks and the depth of the corresponding troughs may gradually decrease in size away from the outer lateral side of the seal section, i.e. the peaks and troughs nearest the centre of the cover (and the other seal section) may have the smallest height and depth. This permits a reliable seal to be formed.

At least one of the longitudinally extending troughs may comprise a longitudinally extending lacuna and the corresponding longitudinally extending peak may comprise longitudinally extending nub (or vice versa). With such an arrangement, in use, a portion of the nub may be received in the lacuna to thereby hold the overlapping seal portions together, i.e. thereby providing a locking means.

The serrations, or undulations, may be uneven. This has the advantage that adhesive and frictional properties may be optimised which can aid liquid dispersal and may provide a low surface area of contact to provide enhanced user comfort and to further minimise damage to damaged skin. The size of the serrations or undulations may differ.

The sections may be formed from a resiliently deformable, flexible polymer with adhesive properties. The seal sections may be formed from thermoplastic elastomer (TPE).

In an embodiment, the seal sections may each comprise two different materials, these may be two different thermoplastic elastomers and these may have been coextruded to form the seal sections. For example, the seal section may comprise a relatively (compared to the other layer) rigid layer and a more flexible layer. The serrations or undulations of the seal sections may be formed of the more flexible layer. This means that the layer in contact with the skin may be more flexible and thus more easily conform to the user's body. This may make the device more comfortable for the user, especially if worn for a long period of time. Additionally, if the device comprises a locking means (e.g. a longitudinal nub and lacuna), this portion of the seal section may be formed from the more flexible material. This may mean the locking means can be more resilient to being pulled apart.

The adhesive properties may include micro-formation of texture or perforation, for example in order to capture moisture and create surface tension. This form of adhesive may be additional or alternative to the inclusion of standard adhesives. For example, it may be required that the user's skin is shaved prior to contact or adhesion.

The seal sections may be extruded as one part with a flat base and plurality of serrations or undulations which are folded and secured around the cover. When the extruded seal section is folded around the cover, it may form two complementary surfaces which, in use, can be mated together to form a seal. The extruded seal sections may include a dedicated central recess for receiving the cover. The seal sections may each be folded around the cover at the recess (i.e. the recess may also act as a hinge) so that the flat base is in contact with both sides of the cover. The seal sections may be welded to the film.

When the seal sections are extruded, the cross-sectional shape of the seal sections will be constant along its length. This means that a skin protection device may be used to wrap around a continuum of different size parts of a user's body. This is because the skin protection device can overlap itself by any length whilst still being capable of forming a seal.

Thus in a second aspect, the present invention provides a skin protection device comprising: a flexible cover having a first end and a second end with two sides extending therebetween, wherein said sides comprise seal sections, wherein said seal sections are capable of mutual engagement to form a seal, wherein each seal section is an extrusion as one part with a flat base and a plurality of serrations or undulations, folded and secured around the sides of the cover so that the flat base is in contact with both surfaces of the cover.

The present invention in a third aspect provides a method of manufacturing a skin protection device, wherein the method comprises: providing a flexible cover having a first end and a second end with two sides extending there between, providing extruded seal sections which are each capable of mutual engagement to form a seal and wherein each seal section is one part with a flat base and a plurality of serrations or undulations, and folding and securing one of the extruded seal sections to each side of the cover so that the flat base is in contact with both surfaces of the cover.

When the seal sections are extruded they may each be coextruded. This means that the seal sections can comprise two different materials which may have different mechanical properties. When the seal sections are extruded as one part with a flat base and a plurality of serrations or undulations it may be coextruded. This means that the base layer which is in contact with the cover when folded around the cover may be more rigid and the serrations and undulations may be more flexible.

In embodiments the seal sections and/or cover may include elasticity, i.e. they may have elastic properties. This means that, for example, the device may be stretched out of shape to accommodate different shaped subordinate skin areas, and may further aid in permitting offset connection of the seal serrations or undulations.

The protective cover, i.e. the skin protection device, may be wrapped around part of the user's body so that it overlaps to form a cuff around the user, for example the protective cover may be wrapped around the user's arm.

In embodiments the seal sections may be capable of adhering through adhesive or through the use of friction to the user's skin so as to be able to prevent the ingress of water into the device during use. The cover's edges in use may form the device top and bottom and include the seal thereby serving to secure the top and bottom to the user's skin.

The cover's front and back edges (first and second ends) having no seal may be positioned to overlap when in use, wherein a back edge is positioned against the skin and a front edge is wrapped around until it overlaps the back edge. The front edge may be stuck to the cover by means of adhesive or sticky tape so as to prevent water ingress.

In some embodiments at least one of the seal sections may include a liquid or heat activated adhesive which serves to seal the sealant strip to the user and to itself when it becomes wet, warm or hot. In embodiments part of the seal may include thermochromic material in addition or the alternative to the liquid or heat activated adhesive.

In some embodiments a pressure sensitive adhesive tape may be used in addition to the seal provided by the seal sections. This can simplify application of the device.

In some embodiments adhesive tape may be used to adhere the cover to the user's skin rather than to itself.

The skin protection device may be arranged so that, once the seal sections have been used to form a mating pair, the seal sections may be disengaged by pulling the overlapping portions of the sealing sections apart. The skin protection device may be reused or alternatively may be a one-use, disposable item.

The device may contain or prevent others from contracting a bacterial infection, filter ultraviolet rays and/or act as a carrier for other chemical based inhibitors, coatings or treatments such as topical treatment layers. The treatments may be integral to a polymer based cover and seal sections, for example, the treatments may be incorporated in a polymer mix or provided as a polymer additive.

The device may reduce the number of times a wound needs dressing, it may keep the wound dry with reduced bacteria, and physically clean from dirt. This is because, at least in a preferred embodiment, the device can provide an effective seal against a user's skin. This means less outpatient or nurse/carer home visits and therefore may have a commercial advantage by reducing demand and resources required for on-going wound maintenance care.

In its broadest aspect, the present invention provides a skin protection device comprising: a flexible cover having a first end and a second end with two sides extending therebetween, wherein said sides comprise seal sections, wherein said seal sections are capable of mutual engagement to form a seal. This aspect of the invention may have one or any combination of the above described features.

BRIEF DESCRIPTION OF FIGURES

A preferred embodiment of the present invention will now be described by way of example only, and with reference to the following figures in which:

FIG. 3 shows a view from above of the embodiment shown in FIG. 1;

FIG. 4 shows a side view of the embodiment shown in FIG. 1;

Figure 1:
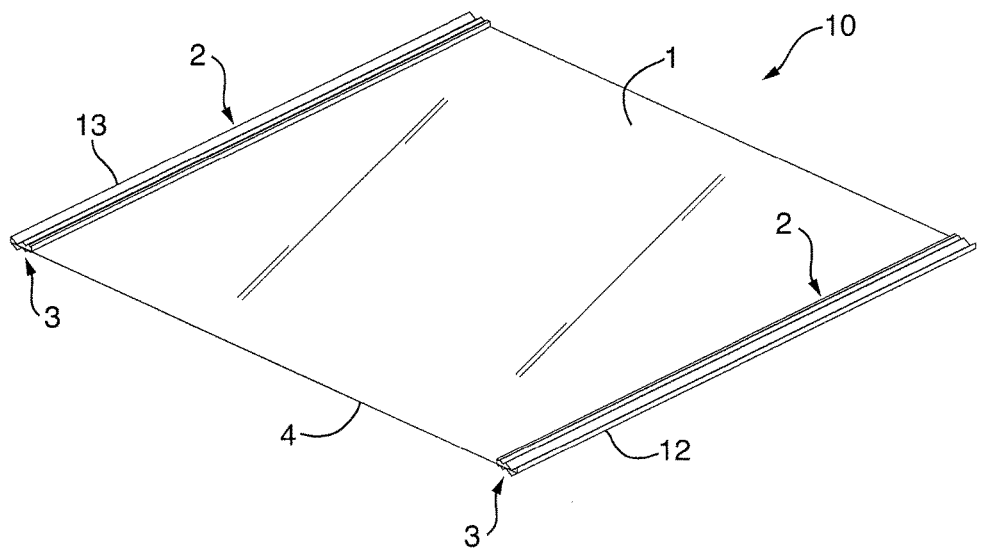
FIG. 1 shows an isometric view of an embodiment of the device before use.

With reference to the figures the skin protection device 10 comprises a cover 11 with a first face 1 and a second face 4. The cover has peripheral, seal sections 12, 13 which each have a first surface 2 and a second surface 3. The first face (i.e. surface) 2 of each of the seal sections is arranged to engage with a second face 3 of that respective peripheral section, to make the seal. The cover 11 may be reversed and each face, 1 or 4, may have different properties. For example, one face 1 or 4 may be provided with a thermochromic, reflective and/or luminescent coating, to be used exterior, or one face 1 or 4 may include antibacterial, hypoallergenic, hygienic or drug based properties to be used interior.

In an embodiment, the cover thickness is no greater than 0.04 mm, and preferably no greater than 0.017 mm, so as to be easily stowed and to be comfortable and flexible in use.

The seal section 12, 13 width (i.e. the transverse dimension) is at least 5 mm, preferably 5-10 mm and preferably no greater than 20 mm so as to enable adhesion of the seal to itself or the user. Preferably the section thickness is no greater than 3 mm, i.e. the dimension from a point on one side of the seal section to the corresponding point on the other side of the seal section is less than 3 mm. The depth with serrations is at least 5 mm and no greater than 10 mm, i.e. the peak to peak dimension is greater than 5 mm and less than 10 mm.

The seal sections 12, 13, each comprise serrations, or undulations. The serrations, or undulations, in preferred embodiments are dimensioned with reference to FIG. 2, wherein a relatively larger trough 7 corresponds with an undulation or serration 8. A series of relatively smaller troughs and peaks follow subsequently, wherein the next trough contains a lacuna 6 corresponding to a nub 5 on the corresponding peak.

Figure 2:
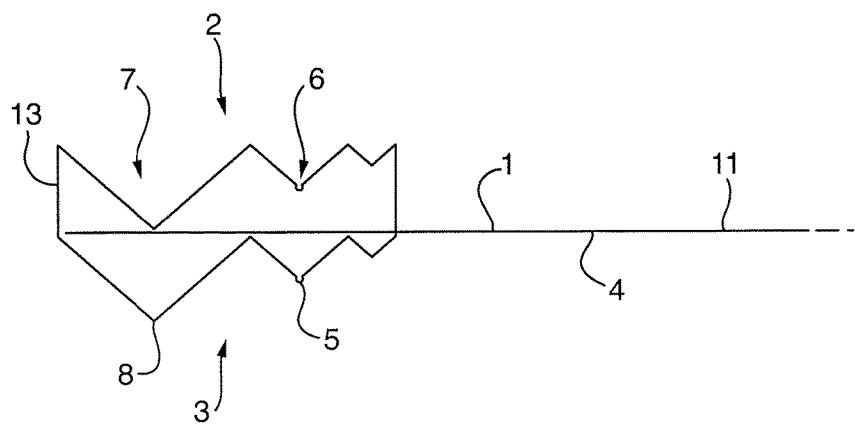
FIG. 2 shows a detail side view of a seal section from the embodiment shown in FIG. 1.

The seal section 13 in the embodiment shown in lateral cross section in FIG. 2 comprises three longitudinally extending peaks on one surface 3 of the seal section and three corresponding longitudinally extending troughs on the other, opposing, surface 2 of the seal section 13. The seal section 13 may comprise any number of corresponding longitudinally extending peaks or troughs.

Figure 5:
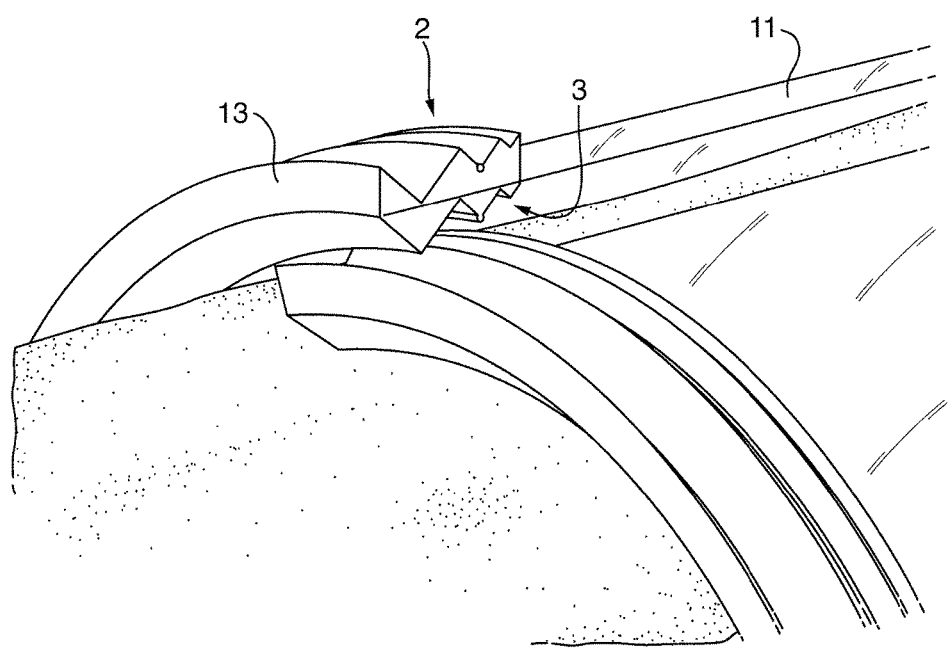
FIG. 5 shows the device wrapped around a part of a patient.

When the skin protection device 10 is wrapped around a part of a user's body (as shown in FIG. 5) a portion of one surface 3 of the seal section 13 will be received in the opposite surface 2 of the seal section 13 to thereby form a seal.

FIG. 6 shows the process of attaching one of the seal sections 12, 13 to the flexible cover 11. FIG. 6a shows a lateral cross-section of the extruded seal section 12, 13. The seal section is extruded as a single piece which comprises a female and a male surface 2, 3. As a result of the seal section 12, 13 being extruded the cross-sectional shape is constant along its length. Half way along the cross-section of the seal section a thin, v-shaped portion 14 (see FIG. 6d) is provided. This v-shaped section 14 acts as a hinge about which the seal section 12, 13 can be folded. Additionally, the v-shaped section provides a recess for receiving an edge of the flexible cover 11.

Figure 6A:
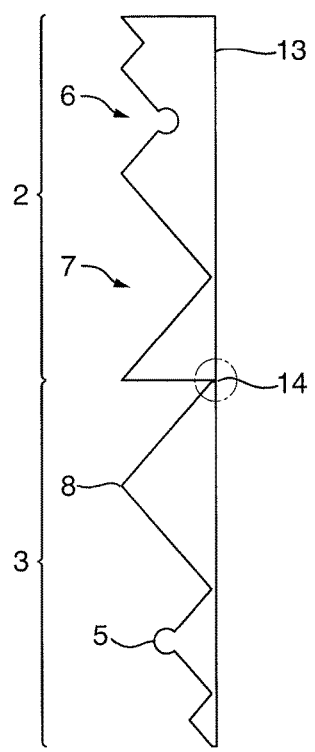
FIG. 6 shows a seal section, in lateral cross section, being attached to a cover.
Figure 6B:
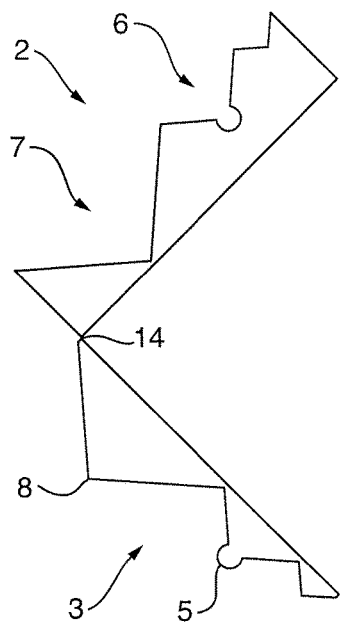
Figure 6C:
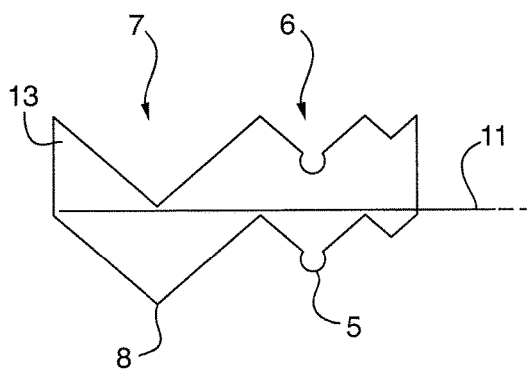
Figure 6D:
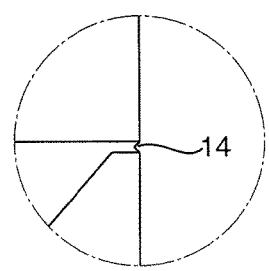

To attach the seal section 12, 13 to the flexible cover 11, the cover is received in the v-shaped recess 14 and the seal section is folded about the v-shaped section so that a flat base of the extruded seal section 12, 13 is in contact with the opposing surfaces of the cover 11 along one side (as shown in FIGS. 6b and 6c). Once folded about the cover 11 the seal section 12, 13 may be secured onto the cover by welding, adhesive or another known attachment means.

The invention has been described by way of example only and it will be appreciated that variations may be made to the above-mentioned embodiments without departing from the scope of invention, which is defined by the appended claims.

With respect to the above description, it is to be realised that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined by the following claims.

The invention claimed is:

1. A skin protection device comprising:
a flexible cover having a first end and a second end with two sides extending therebetween, wherein each of said sides comprises a seal section,
wherein each of said seal section is capable of mutual engagement with itself to form a seal,
wherein each said seal section includes a surface that is longitudinally serrated or undulating,
wherein serration or undulation is provided on both an upper surface of the seal section and a lower surface of the seal section opposite the upper surface to provide a first female serrated or undulating surface and a second male serrated or undulating surface which when placed together form a mating pair and the seal,
wherein the skin protection device is configured such that when it is wrapped around a part of a user's body, the serration or undulation of one of the first female serrated or undulating surface and the second male serrated or undulating surface of each seal section contacts the user's skin in order to form a seal with the user's skin, and
wherein the skin protection device is configured to overlap itself by any length while still being capable of forming the seal.

2. The device according to claim 1, wherein each said seal section is an extrusion as one part with a flat base and a plurality of serrations or undulations, wherein each seal section is folded and secured around one of the sides of the cover so that the flat base is in contact with the upper surface and the lower surface of the cover.

3. The device according to claim 1, wherein the cover comprises hydrochromic means.

4. The device according to claim 1, wherein the female surface comprise a plurality of troughs and the male surface comprises a plurality of corresponding peaks, and wherein a first trough is deeper than a second trough.

5. The device according to claim 1, wherein the seal sections are arranged in use to adhere to skin through friction.

6. The device according to claim 1, wherein each said seal section comprises a nub and a corresponding lacuna locking means.

* * * * *